United States Patent [19]

Taylor

[11] Patent Number: 4,580,453

[45] Date of Patent: Apr. 8, 1986

[54] GEAR CASE OIL SAMPLER

[76] Inventor: Julian S. Taylor, 8300 SW. 8, Oklahoma City, Okla. 73128

[21] Appl. No.: 670,838

[22] Filed: Nov. 13, 1984

[51] Int. Cl.⁴ .............................................. G01N 1/14
[52] U.S. Cl. ............................ 73/863.86; 73/863.84; 73/863.85; 73/864.62; 73/864.63; 73/864.34
[58] Field of Search ........... 73/864.62, 864.51, 864.34, 73/864.35, 864.63, 864.86, 863.85, 863.83, 863.84; 74/606 A; 184/1.5

[56] References Cited

U.S. PATENT DOCUMENTS

| | | | |
|---|---|---|---|
| 2,352,234 | 6/1944 | Swearingen | 73/863.86 X |
| 3,011,349 | 12/1961 | Kratz | 73/863.86 |
| 3,541,860 | 11/1970 | George | 73/863.83 |
| 3,638,499 | 2/1972 | Saint-Andre | 73/863.86 |
| 3,930,413 | 6/1976 | Laird et al. | 73/863.85 |
| 4,056,981 | 11/1977 | Kelka et al. | 73/863.85 |
| 4,150,575 | 4/1979 | Magorien | 73/863.86 |
| 4,289,027 | 9/1981 | Gleaves et al. | 73/863.86 X |
| 4,423,641 | 1/1984 | Ottung | 73/863.86 |
| 4,524,811 | 6/1985 | Taylor | 184/1.5 X |
| 4,548,088 | 10/1985 | Hood, Jr. | 73/864.34 |
| 4,549,440 | 10/1985 | Fournier et al. | 73/863.85 |

FOREIGN PATENT DOCUMENTS

| | | | |
|---|---|---|---|
| 2143045 | 3/1972 | Fed. Rep. of Germany | 73/863.83 |
| 2819554 | 11/1979 | Fed. Rep. of Germany | 73/864.62 |
| 763726 | 9/1980 | U.S.S.R. | 73/864.62 |

Primary Examiner—Stewart J. Levy
Assistant Examiner—Tom Noland
Attorney, Agent, or Firm—Robert K. Rhea

[57] ABSTRACT

In a gear case oil sampling device for use with a gear case containing a quantity of lubricating oil, an axially bored access plug is connected with the gear case. The plug includes an oil tube immersed in the lubricating oil when the gear system is idle and an air core valve normally closes the plug bore. An oil sample container slidably surrounds a piston for longitudinal movement of the container relative to the piston. An axially bored piston rod projects out of the container open end and is connectable with the access plug in a plug valve opening manner to provide fluid communication between the container and the gear case oil. A one-way clutch connects the open end of the container with the piston rod to permit manual movement of the container relative to the piston rod in one direction and reduction below atmospheric pressure in the container closed end portion.

8 Claims, 6 Drawing Figures

GEAR CASE OIL SAMPLER

BACKGROUND OF THE INVENTION

1. Field of the Invention

The present invention relates to off-the-road vehicles and general machines and more particularly to a device for obtaining a sample of the gear system lubricating oil when the vehicle or machine is idle.

In the maintenance of large machinery it is common practice to obtain a sample of the gearbox lubricating oil for analysis. By analyzing the various elements in suspension in the oil a determination is made of the worn condition of the gear reduction parts and when it is necessary that maintenance repairs be made or when an overhaul of the gear system is required.

2. Description of the Prior Art

In obtaining samples of gear system lubricating oil it has been common practice to insert a tube into the gear system lubrication area through the oil fill access opening while the vehicle or machine is idle. The inserted tube is connected with a pressure reducing bulb or apparatus for drawing a quantity of the gear lubricant out of the oil bath case which is received by a suitable receptacle. This procedure has the disadvantage of contaminating the gear case by other impurities not normally present in the gear lubricating oil, when access ports are opened for sampling. Further, the sample device is frequently used for successively containing a plurality of gear case oil samples thereby transferring some of the impurities from one gear case oil sample to another by the sampling device. Additionally, such a sample obtaining apparatus is not usually capable of being sealed, as a separate unit, while awaiting its turn for the analyzing function. Also, sampling should be done from the same reference point in the gear case. This sampling point should not be at the discretion of the individual doing the sampling.

This invention is distinctive over the present procedure by providing an oil sample containing device which is relatively inexpensive and therefore may be discarded after a one time use, one of the devices being used for each gear case oil sample obtained. Further, the device operates by pressure differential in combination with an access plug permanently installed on the gear case which seals fluid tight after obtaining an oil sample.

SUMMARY OF THE INVENTION

In the preferred embodiment of the invention, a centrally bored valve closed access plug is retrofitted on a gear case or installed at the time of manufacture in place of the conventional gear case oil fill plug. The access plug features an outwardly projecting air core closed valve body communicating with the gear case oil through an oil tube projecting from the valve body into the gear case oil. An elongated cylindrical container, having one closed end, is axially connected with a centrally bored one-way clutch. The container slidably receives a piston having the rod thereof slidable in the bore of the clutch. The piston and rod are centrally bored and the rod is provided with threads at its end opposite the piston for connection with the access plug valve body. A depressor tube, projecting out of the piston rod bore, opens the core valve in the access plug. When the container is moved longitudinally relative to the piston and rod, a partial vacuum chamber is formed in the container closed end portion and oil flows through the access plug and piston rod and into the container. The one-way clutch maintains the container extended relative to the piston until the container is filled or the piston rod released from the access plug.

The principal object of this invention is to provide a gear case oil sampling device for removing oil from a gear case or a drive train while the gears are idle by a pressure differential and which prevents environmental contamination of the gear case oil or the oil sample.

DESCRIPTION OF THE PREFERRED EMBODIMENTS

Figure 1:
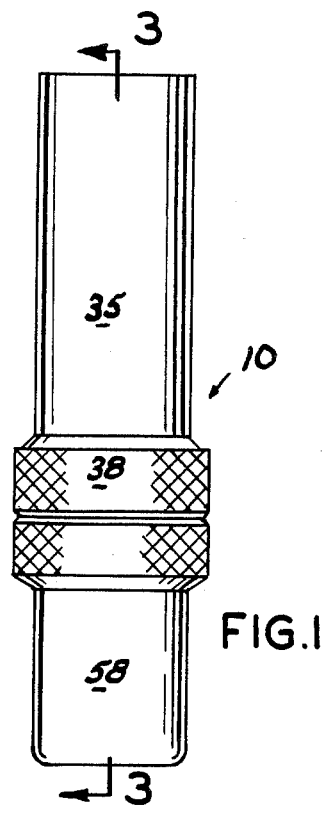
FIG. 1 is an elevational view of the oil sampling container.
Figure 2:
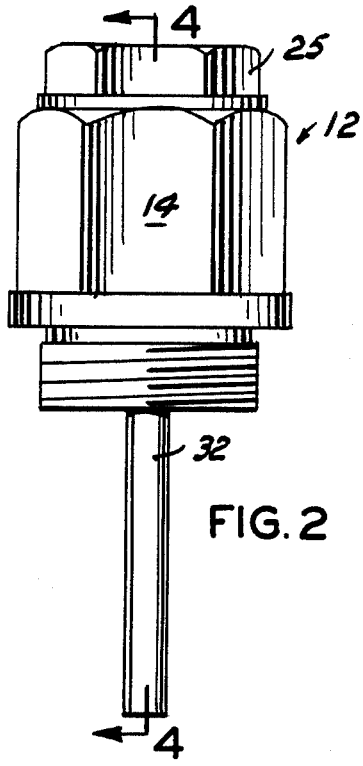
FIG. 2 is an elevational view of the gear case oil access plug.
Figure 3:
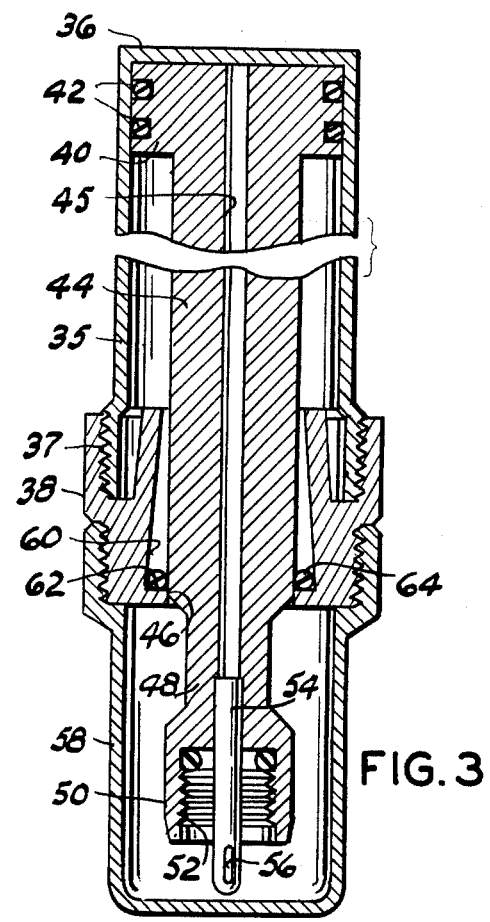
FIGS. 3 and 4 are vertical cross sectional views, to a larger scale, taken substantially along the lines 3—3 and 4—4 of FIGS. 1 and 2, respectively.
Figure 4:
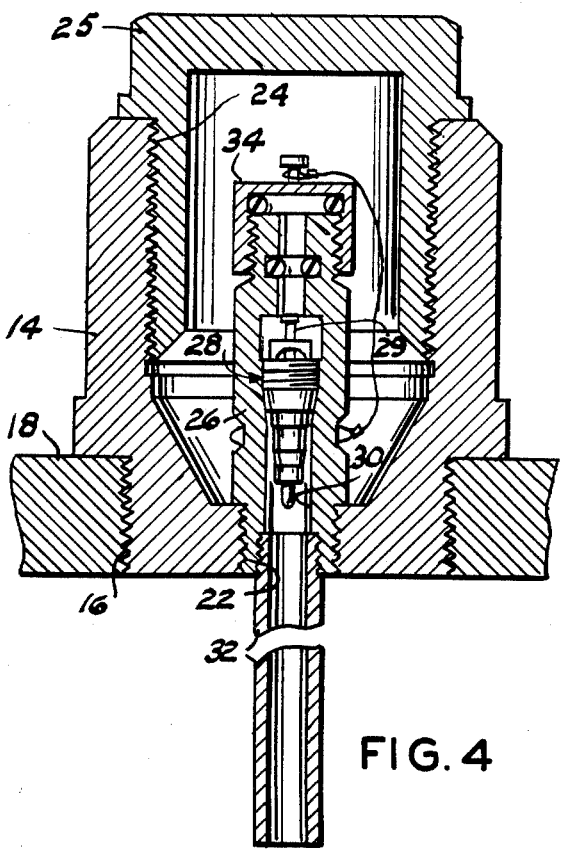
Figures 5, 6:
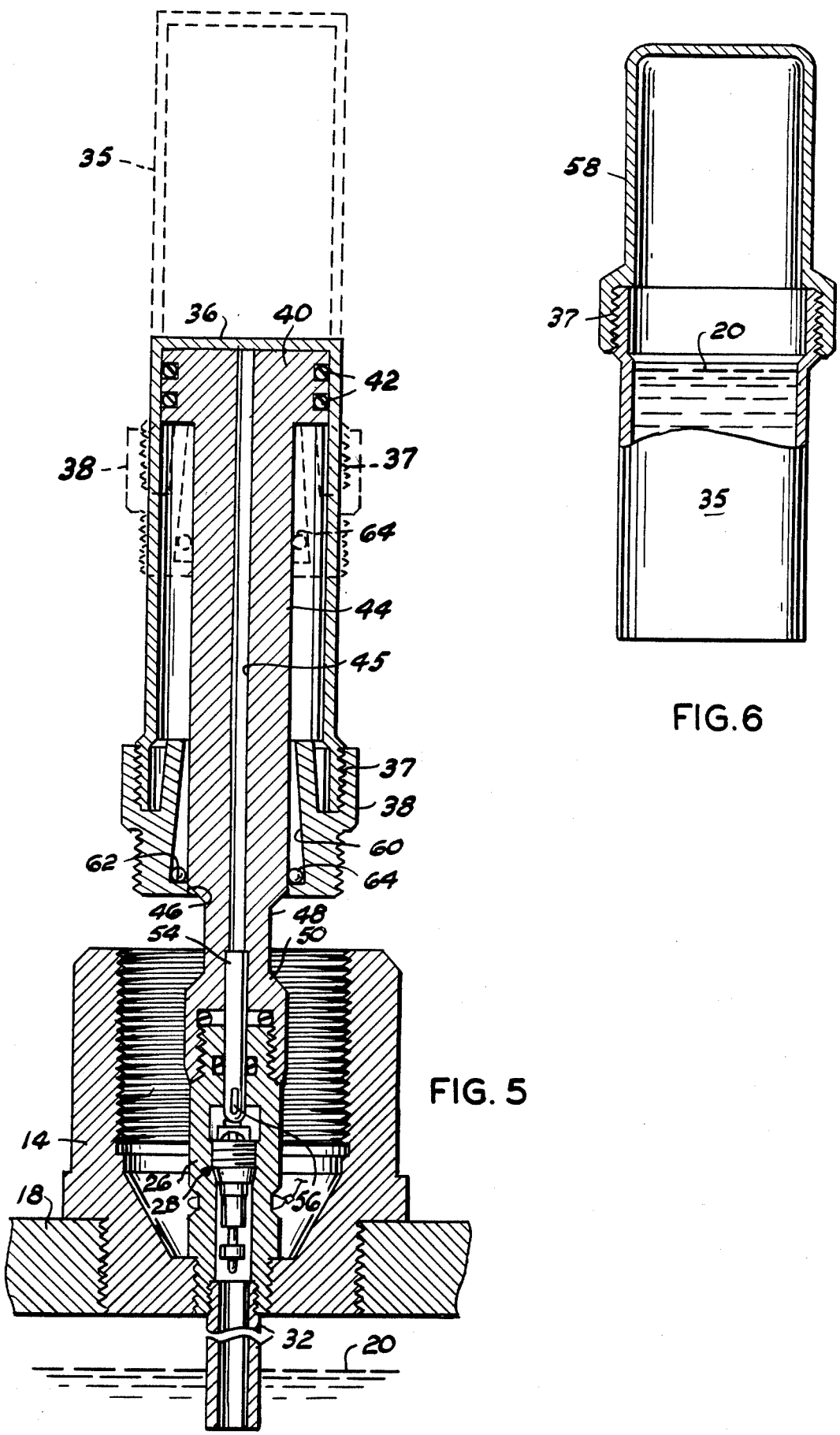
FIG. 5 is a view similar to FIGS. 3 and 4 illustrating the container and access plug in operative position with the partial vacuum forming action shown by dotted lines; and, FIG. 6 is a cross sectional view, partially in section, inverted from the position of FIG. 5 and illustrating the final configuration of the container and its oil sample.

Like characters of reference designate like parts in those figures, of the drawings in which they occur.

In the drawings:

The reference numeral 10 indicates the oil sample container, per se, which is cylindrical in general configuration. The reference numeral 12 indicates a cylindrical access plug providing communication between the oil sample container 10 and oil in a gearbox of gear case to be tested.

The plug 12 comprises a body portion 14 having an externally threaded diametrically reduced end portion 16 which is received by the threaded bore formed in the wall 18 of a gear case containing oil 20 normally containing a gear case oil fill plug, not shown. The plug 12 is centrally bored and threaded at its inward end, as at 22, and counterbored and threaded, as at 24, at its other end portion. The counterbore 24 is closed by a plug cap 25. The threaded bore 22 receives a centrally bored valve body 26 projecting into the counterbore 24 and which is provided with a conventional air core valve 28 to normally close the valve body bore 30 but permit access to the gear oil by the oil sampler.

The valve 28 is preferably the type presently used as an air valve in closing large pneumatic tire valve stems. A longitudinally moveable valve rod 29 is spring biased to normally close the valve 28. The inward end portion of the bore 30 of the valve body 26 threadedly receives one end portion of an oil tube 32 having a length selected in accordance with the gear case on which the plug 12 is installed and in which the end of the tube opposite the valve body is immersed in the oil 20 when the gear system is idle. The outward end of the valve body 26 is normally closed by a valve cap 34.

The oil sample container 10 comprises a tubular container 35 having an end wall 36 with its opposite open end threaded, as at 37, and axially connected with a one-way clutch 38. The inner wall surface of the tubular container 35 receives a piston 40 having surrounding O'rings 42 to form a fluid tight seal with the container wall. A piston rod 44, having an axial bore 45 extending through the piston, projects axially through the container and the bore 46 of the one-way clutch. The piston rod is further characterized by a reduced neck portion 48 adjacent the clutch 38 and opposite the piston 40 which may be provided with wrench fits, not shown, for the purpose believed presently apparent. The neck 48 defines the limit of inward movement of the piston into the container relative to the clutch and defines a piston rod end portion 50 having a threaded counterbore 52 for connection with the valve body 26 after removing its cap 34, as presently explained.

A relatively small diameter sleeve 54, having one closed end, is coaxially inserted at its other end portion into the piston rod bore 45 at the piston rod end portion 50. The closed end of the sleeve projects axially beyond the counterbore 52 and is provided with at least one slot 56 in its wall adjacent its closed end. The purpose of the sleeve closed end is to depress the valve rod 29 to open the valve 28 and admit oil to the container, as presently explained.

A container cap 58, threadedly connected with the clutch 38, surrounds the outward projecting end of the piston rod and is dimensioned to serve as a cap for the container 35 by engaging the container threads 37 after removing the clutch, as presently described.

The clutch is characterized by a tapered bore 60 inclined or diverging with respect to the longitudinal axis of the piston rod toward the free end of the piston rod to define an annular shoulder 62 normal to the clutch bore 46. A plurality of balls 64 are disposed in the annulus generated by the tapered bore 60 adjacent the piston rod and are normally in contact with the shoulder 62 when the piston 40 is moved relative to the container 35 toward the clutch 38. The balls 64 form the one-way clutch action by wedging between the periphery of the piston rod and inner tapered wall surface 60 when the piston is biased, by pressure differential at opposite ends of the piston, toward the container closed end 36 after the container and clutch have been manually moved longitudinally as a unit relative to the piston in a direction opposite to the access plug 12.

OPERATION

In operation, assuming the access plug 12 has been installed on the gear case in which it is desired to sample the oil, the access plug 25 is removed and the valve body cap 34 is similarly removed. The container end cap 58 is also removed. The piston rod end portion 50 is threadedly engaged with the exposed end portion of the valve body 26 which forces the closed end of the tube 56 against the valve rod 29 to depress the latter and open the valve body bore 30. Other O'rings, contained by the valve body 26 and piston rod end portion 50, respectively, insure a fluid and airtight seal. This provides communication between the closed end 36 of the container and the gear case chamber through the oil tube 32, valve 28, tube 54 and piston rod bore 45.

The container 35 is manually grasped and moved longitudinally relative to the piston 40 and its rod in a direction away from the access plug 12. This reduces the pressure below atmospheric pressure in the container 35 between its closed end 36 and the piston 40 so that oil 20 is drawn from the gear case into the partial vacuum chamber. Movement of the container 35 relative to the piston is limited to the spacing between the piston and the one-way clutch member 38 when the latter is disposed adjacent the piston rod neck 48.

When the container closed end has been moved a selected distance from the piston 40 and released, the clutch balls 64, by frictionally engaging the periphery of the piston rod 44 and tapered inner wall surface 60 of the one-way clutch bore, frictionally hold the one-way clutch against movement relative to the piston rod.

After the vacuum chamber has been filled with oil, the device 10 is removed from the access plug by unscrewing the piston rod end portion 50. Filling of the vacuum chamber with oil has equalized the pressure on opposite sides of the piston thus permitting this action. The one-way clutch is unscrewed from the container 35 and removed with the piston and its rod. The clutch end cap 58 is then threadedly connected with the container threads 37 to seal the oil therein. The access plug caps 25 and 34 are reinstalled.

The plug 12 is easily removed from the gear case for testing the oil level therein and adding oil when needed.

Obviously the invention is susceptible to changes or alterations without defeating its practicability. Therefore, I do not which to be confined to the preferred embodiment shown in the drawings and described herein.

I claim:

1. In a gear case containing a quantity of lubricating oil and having a valve closed access plug normally closing an opening in a wall of the gear case and communicating with the oil, the improvement comprising:

container means having opposing ends for receiving an oil sample;

means including a piston rod rigidly connecting one end of said container means said access plug for providing communication between said container means and the gear case oil; and, means including a piston for reducing the pressure in the end portion of said container means opposite the access plug below atmospheric pressure, said container means being manually moveable longitudinally relative to said piston.

2. The combination according to claim 1 in which said piston rod is connected with said piston and said piston rod is characterized by a longitudinal bore extending through said piston.

3. The combination according to claim 2 in which said connecting means further includes:

access plug valve opening means including a tubular member supported by said piston rod.

4. The combination according to claim 3 and further including:

clutch means connecting said container means with said piston rod in a manner permitting movement of said container means relative to the piston in only one direction.

5. Apparatus for obtaining a sample of gear case oil, comprising:

axially bored plug means adapted to be secured to a gear case containing oil for communicating with the oil;

valve means for opening and closing the plug means bore;

container means having opposing ends for holding an oil sample;

means including a piston rod rigidly connecting one end of said container means with said plug means for establishing fluid communication between the container means and the gear case through said plug means; and, means including a piston for reducing the pressure in the end portion of said container means opposite the access plug below atmospheric pressure.

6. The apparatus according to claim 5 in which said piston rod is connected with said piston and said piston rod is characterized by a longitudinal bore extending through said piston.

7. The apparatus according to claim 6 and further including:

valve depressor means including a tubular member supported by said piston rod for opening said valve means.

8. The apparatus according to claim 7 and further including:

clutch means connecting said container means with said piston rod in a manner permitting manual movement of said container means relative to the piston rod in only one direction.

* * * * *